United States Patent [19]

Bayless et al.

[11] Patent Number: 4,902,718

[45] Date of Patent: Feb. 20, 1990

[54] CALCIUM HOMEOSTASIS COMPOSITIONS AND METHODS FOR CONTROLLING CALCIUM METABOLISM

[76] Inventors: Robert K. Bayless, 6509 Pevensey Dr., Austin, Tex. 78745; Gerald P. Hirsch, 8414 Hanbridge La., Austin, Tex. 78736; Sandra S. Kern, 2630 Deerfoot Trail, Austin, Tex. 78704

[21] Appl. No.: 179,258

[22] Filed: Apr. 8, 1988

[51] Int. Cl.[4] .......................................... A61K 31/195
[52] U.S. Cl. .................................... 514/562; 514/877; 514/871; 514/904; 514/905
[58] Field of Search ............... 514/904, 905, 891, 877, 514/562

[56] References Cited

U.S. PATENT DOCUMENTS

| | | | |
|---|---|---|---|
| 2,456,820 | 1/1949 | Howe et al. | 514/562 |
| 3,773,930 | 11/1973 | Mohammed et al. | 514/60 |
| 4,315,028 | 2/1982 | Scheinberg | 424/290 |
| 4,409,233 | 10/1983 | Tsukada et al. | 514/562 |
| 4,499,076 | 2/1985 | Ohashi et al. | 514/54 |
| 4,649,040 | 3/1987 | Ditha | 514/562 |
| 4,711,780 | 12/1987 | Fahim | 514/562 |

FOREIGN PATENT DOCUMENTS 2618099  11/1977  Fed. Rep. of Germany .

OTHER PUBLICATIONS

Chemical Abstracts 97:178781w (1982).
Donland's *Medical Dictionary*, p. 217 (1957).
*Current Therapy*, pp. 456–457 (1984).
*Facts and Comparisons*, pp. 54–55 (1983).
*Physician's Desk Reference*, 31st Ed. (1977), pp. 1127 and 1134.
*Handbook of Non-Prescription Drugs*, 8th Ed. (1987), p. 216–220.
Smolin et al., "The Use of Betaine for the Treatment of Homocystinurea" Journal Ped, Sep. 1981.
Johansson et al.; *The Journal of Urology*, "Biochemical and Clinical Effects of the Prophylactic Treatment of Renal Calcium Stones With Magnesium Hydroxide", 1980, pp. 770–774.
Preminger et al.; *the Journal of Urology*, "Prevention of Recurrent Calcium Stone Formation With Potassium Citrate Theraphy in Patients With Distal Renal Tubular Acidosis", vol. 134, pp. 20–23.
Pak et al.; *the Journal of Urology*, "Long-Term Treatment of Calcium Nephrolithiasis With Potassium Citrate", vol. 134, pp. 11–19.
Thornton; *Current Veterinary Therapy IV*, "Urinary Calculi In the Dog", 1971, pp. 695–706.
Cuperus et al.; Arthritis and Rheumatism, "Antiarthritic Drugs Containing Thoiol Groups Scavenge Hypochlorite and Inhibit Its Formation By Myeloperoxidase From Human Leukocytes", vol. 28, No. 11, November 1985, pp. 1228–1233.
Cho et al.; *Journal of Parenteral and Enternal Nutrition*, "D-Methionine Utilization in Young Miniature Pigs, Adult Rabbits, and Adult Dogs", vol. 4, No. 6, pp. 544–547.
Stegink et al.; *Journal of Nutrition*, "Plasma Methione Levels in Normal Adult Subjects after Oral Loading with 1-Methionine and N-Acetyl-1-Methionine", 1980, pp. 42–49.
Rotruck and Boggs; *Journal of Nutrition*, "Comparative Methionine", 1975, 105:pp. 331–337.
Tietz; *Fundamentals of Clinical Chemistry*, "Blood Gasses and Electrolytes", "Analysis of Calculi", 1976, pp. 901–903, pp. 1015–1025.

*Primary Examiner*—Stanley J. Friedman
*Attorney, Agent, or Firm*—J. F. Long

[57] ABSTRACT

This invention concerns novel calcium normalizing compositions containing as the active agent the amino acid methionine, and/or one or more related compounds including certain metabolic precursor compounds, and novel methods employing the compositions for normalizing or controlling calcium metabolism. The compounds include the methionine hydroxy analog, the S-methyl methionine analog, and methionine compounds having the structural formula I

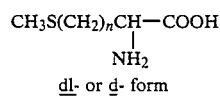

$$CH_3S(CH_2)_nCH-COOH \quad\quad I$$
$$\underset{\underline{dl}\text{- or }\underline{d}\text{- form}}{|\ NH_2}$$

and pharmaceutically acceptable N- (mono- and dicarboxylic acid) acyl derivatives and alkyl esters thereof, where in is an integer from 1 to 3.

9 Claims, No Drawings

CALCIUM HOMEOSTASIS COMPOSITIONS AND METHODS FOR CONTROLLING CALCIUM METABOLISM

TECHNICAL FIELD

This invention concerns novel calcium metabolism normalizing compositions containing the amino acid methionine (also known as "Met"), and/or one or more related compounds including certain metabolic precursor compounds, and novel methods employing the compositions for normalizing or controlling calcium metabolism.

BACKGROUND OF THE INVENTION

Solid calcium deposits, urinary calculi and kidney stones have been a significant medical problem for many years. Despite recent progress in sonic disruption of stones, safe chemical treatment and prevention are still preferred. Current chemical therapy utilizes potassium citrate or magnesium administration to prevent calcium stone formation (Johansson et al., J. Urology, 124: 770–774, 1980; Preminger et al., ibid. 134:20–23, 1985; Pak et al., ibid. 134:11–19, 1985).

Methionine has been prescribed for control of urinary pH in dogs and cats and has been effective in reducing the occurrence of both bladder and kidney stones in dogs (Thornton, Current Vet. Therapy IV, 695–702, 1971). dl-Methionine is effective in cats to maintain the urinary pH at 6 (Rich, Current Vet. Therapy IV, 703–706, 1971).

Differences exist in the relative effectiveness of methionine compounds and other chemicals especially in sulfhydryl reducing substances. These differences may be attributed to the control mechanisms that operate in animals and man to regulate the amounts of these substances wherein giving more of a substance does not significantly increase blood and tissue levels of that substance. Stegink, J. Nutrition, 116:1185–1192, 1986, showed that 0.5 gm of methionine elevated total blood methionine two-fold for 2 hours with l-methionine but three-fold for 4 hours with d-methionine.

Regarding human nutrition, l-methionine is an essential amino acid whereas d-methionine is not essential. For purposes of metabolism, l-methionine via S-adenosylmethionine has an important methylating function. In this function it loses a methyl group from its sulfur atom to become homocysteine. Homocysteine, as is known, when in excess can lead to homocysteinuria and may in excess be disease associated.

Cuperus, Arthritis and Rheumatism, 28: 1128–1233, 1985, describes a feature of inflamed synovial fluid, such as that occurring in arthritis patients, as the accumulation of polymorphonuclear (PMN) leukocytes. One function of the leukocytes is the destruction of invading elements such as microorganisms. For this destruction, the leukocyte releases hydrogen peroxide and enzymes, e.g., myeloperoxidase, into the extracellular fluid. In the presence of hydrogen peroxide and chloride ion, myeloperoxidase catalyzes the formation of reactive hypochlorous acid (HOCl) which can oxidize tissue components and plasma protease inhibitors. Oxidation and subsequent inactivation of these protease inhibitors in vivo may lead to unrestrained proteolysis, resulting in severe tissue damage. dl-Methionine is available as a one-a-day food supplement in 500-mg. oral tablet form. The normal serum level of methionine in man is 15 ppm.

Different species utilize d-forms of amino acids to different extents. Humans and monkeys utilize d-methionine poorly while pigs, dogs, rabbits, chickens and rats utilize d-methionine as a sulfur source fairly well. Animals do not metabolize N-blocked-d-methionine as they do N-blocked-l-methionine. Some N-blocking groups are not cleaved by enzymes that remove common blocking groups such as acetyl groups (Cho, J. Parenteral and Enteral Nutrition, 4: 544–547, 1980; Stegink, J. Nutr. 110: 42–49, 1980; Rotruck, J. Nutr. 105: 331–337, 1975.)

The Scheinberg U.S. Pat. No. 4,315,028 describes a method of treatment of arthritis employing substituted cysteines.

U.S. Pat. No. 3,952,115 describes foodstuffs containing N-acyl l-methionine esters and N-acyl l-cysteine esters.

There is a need at present for means of treating disease conditions presenting as solid calcium deposits, calculi, kidney stones, hypocalcemia, hypercalcemia, urinary calcium and the like (for normal calcium values and methodology, and incorporated herewith, refer to Tietz, Clinical Chemistry, 901 et seq. and 1015 et seq., Saunders Co., 1976).

It is therefore an object of the present invention to provide compositions for consumption or administration and treatment, for normalizing calcium metabolism and alleviating disease conditions of the kind described.

It is also an object of the invention to provide methods for normalizing calcium metabolism and alleviating these disease conditions.

It is a further object of the invention to provide means for preventing or alleviating symptoms of homocysteinuria that may result from excess methionine intake.

These and other objects, features and advantages will be seen from the following detailed description of the invention.

SUMMARY AND DETAILED DESCRIPTION OF THE INVENTION

Our invention is based on the discovery that certain methionine compounds in the dl-form or d-form at relatively high, well-tolerated doses are potent calcium metabolism normalizing agents. The compounds are especially important when consumed or administered or used for treatment in dosage form, for normalizing the calcium metabolism thus lowering or raising, as the case may be, the calcium metabolism i.e. serum calcium, urinary calcium etc., so that in one application growth of calculi is inhibited and in another application resorption of calcium from the bone is reversed or inhibited.

For purposes of the invention, one uses in the dl- or d-form at least one methionine-type compound selected from the methionine hydroxy analog, the S-methyl methionine analog, and methionine compounds having the structural formula I

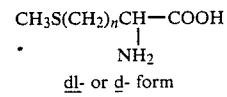

$$CH_3S(CH_2)_nCH-COOH \atop | \atop NH_2$$

dl- or d- form and pharmaceutically acceptable N-(mono- and dicarboxylic acid) acyl derivatives and alkyl esters thereof, where n is an integer from 1 to 3.

Thus, the methionine-type compound (for convenience sometimes referred to herein as "methionine" or "methionine compound") may be normethionine (n=1), methionine (n=2), homomethionine (n=3), the hydroxy analog, the S-methyl methionine analog (also known as vitamin U), or the acyl or alkyl ester derivative thereof, as defined. Exemplary acyl derivatives are the formyl, acetyl, propionyl, and succinyl derivatives, of which the formamide, acetamide and succinyl derivatives are preferred. Exemplary ester derivatives are the methyl, ethyl and isopropyl esters.

In one preferred aspect, the invention concerns a method for normalizing calcium metabolism in a subject. The method comprises administering to the subject a composition or serving in dosage form containing an effective calcium metabolism normalizing amount of at least one methionine compound as defined above. Preferably for this purpose, the methionine compound is administered in a daily dosage, preferably in the range from 20 to 400 mg/kg of body weight, and is continued daily until the calcium metabolism level is normalized. A preferred treatment regimen is a daily oral dose of methionine, preferably 20 to 30 mg/kg of body weight, taken three times in spaced equal doses or in a single equivalent sustained release dosage form. Preferably, for a calcium-deficient subject the dosage form includes as a separate active agent a pharmaceutically acceptable calcium substance such as calcium carbonate, in a recommended daily dosage (for detail concerning agents and dosage involved in regulation of calcium, refer to Nurse's Guide to Drug Therapy, Chapter 85, page 603 et seq., Prentice-Hall, Inc., Englewood Cliffs, N.J., 1984-1985, incorporated herewith by reference).

The method and composition aspects wherein in a preferred embodiment comprise administering in the dosage form with the methionine content at least one homocysteine reducing or remethylating compound sometimes referred to herein as a homocysteine affecting compound. The homocysteine affecting compound is at least one amino acid or nutrient selected from betaine, glycine, serine, vitamin B12, vitamin B6, and folic acid or folate, the compound being present in an amount sufficient to enable the systemic conversion of homocysteine to methionine or cysteine. The metabolic pathways for such conversion are detailed in Lehninger's Biochemistry, 2nd Ed., Chapter 25, Worth Publishers, Inc., 1978, incorporated herewith by reference. Background for this is that methionine may have an adverse effect when given to subjects with vitamin B12 or folate deficiency. This effect is thought to be due to a buildup of systemic homocysteine; homocysteine is poorly remethylated in the absence or deficiency of vitamin B12 or folate. Also, the vitamin B6 level may be too low for the metabolism of homocysteine to cysteine by way of cystathionine. Thus, chronic consumption of excess l-methionine, for example, may result in mild homocysteine elevation unless other co-factor substances are used or supplemented to stimulate the transformation of the excess homocysteine. The buildup is avoided, according to the invention, by including at least one homocysteine affecting compound in the dosage: betaine in an amount such that homocysteine is remethylated to methionine; glycine or serine to insure that homocysteine can be reduced by way of cystathionine to cysteine; vitamin B12 and/or folate to insure that homocysteine can be systemically remethylated; and vitamin B6 to insure that homocysteine can be metabolized to cysteine. The amino acids betaine, glycine and serine preferably are each present in the dosage in an amount from 1/10 to 10 times the amount of the methionine compound, preferably betaine and preferably an equal amount of betaine. The nutrients vitamins B12, B6 and folate preferably are each present in the recommended daily allowance (RDA).

In another preferred aspect, the invention concerns a method for treating the symptoms of calcium-deficiency hypertension in a subject. The method comprises administering a composition or serving to the subject in dosage form containing an effective calcium metabolism normalizing amount of at least one methionine compound as defined above. Preferably for this purpose, the methionine compound is administered in a daily dosage ranging from 10 to 200 mg/kg of body weight and is continued daily until the calcium metabolism is normalized. In a preferred embodiment, the dl-form of methionine is used, preferably in a daily oral dose of 30 mg/kg taken three times in spaced equal doses. The dl-form is preferred because the lcomponent thereof can be converted to taurine, and 40% of the d-component is excreted in the urine. Preferably, the daily dosage of methionine includes a calcium agent or substance as defined above.

In another preferred aspect, the invention concerns a method for inhibiting growth of calculi in a subject. The method comprises administering a composition or serving in dosage form containing an effective calcium metabolism normalizing amount of a methionine compound as defined above. Preferably, the methionine compound is administered in a daily dosage preferably ranging from 10 to 200 mg/kg of body weight and is continued daily until the calcium metabolism is normalized. A preferred treatment regimen is a daily oral dose, preferably 20 to 30 mg/kg of body weight, taken three times in spaced equal doses or in a single equivalent sustained release dosage form.

In another preferred aspect, the invention concerns a method for treating in a subject calcium-deficiency osteoporosis or an osteoporosis resulting from overactive monocytes (Mundy et al., Science, 196: 1109–1111, 1977). The method comprises administering a composition or serving to the subject in dosage form containing an effective calcium metabolism normalizing amount of at least one methionine compound as defined above. For this purpose, the methionine compound preferably is administered, preferably in the dl-form, preferably in a daily dosage, preferably ranging from 10 to 200 mg/kg, and is continued daily until the calcium metabolism is normalized. A preferred treatment regimen is a daily oral dose, preferably 20 to 30 mg/kg of body weight, taken three times in spaced equal doses or in a single equivalent sustained release dosage form. In a preferred embodiment, the dosage form includes the recommended daily dosage of a pharmaceutically acceptable calcium agent or substance as defined above.

In another preferred aspect, the invention concerns a composition for consumption by or systemic administration to a subject for normalizing calcium metabolism in the subject. The composition comprises in dosage form (a) an effective calcium metabolism normalizing amount of methionine, and (b) a recommended daily dosage of a pharmaceutically acceptable calcium agent, and/or (c) at least one homocysteine affecting compound as defined above. Preferably, the composition contains betaine, glycine and serine. Preferably, the amount of the amino acid dosage present is from 1/10 to 10 times the amount of the methionine compound.

The effectiveness of dl-methionine in reducing urinary calcium has been demonstrated. Typically, a person with high urinary calcium and kidney stones but normal acid pH of 6, who consumes 0.5 gm of dl-methionine twice per day for more than two weeks will show reduced insoluble urinary calcium. The invention contemplates that similar doses will improve the calcium levels of older women that would otherwise suffer calcium loss of osteoporosis, and men with high blood pressure that results from low calcium consumption. Humans excrete d-methionine after consumption of dl-methionine but it is not clear whether this excretion is due to a reduced capacity of the kidney to resorb the d-form or whether the limited metabolism of the d-form causes its eventual excretion despite some resorption (Efron et al, American J. Dis. Child., 117: 104–107, 1969; Stegink, Clin. Nutrition Update, 198–205, 1977). Methionine has a slight effect in reducing the insolubility of calcium phosphate at pH 6.5. This effect on solubility is not enough to explain the reduction of insoluble calcium in individuals taking dl-methionine.

PREPARATION OF PHARMACEUTICAL COMPOSITIONS

When being utilized as pharmacological agents, the compositions of the invention can be prepared and administered in a wide variety of topical, oral, and parenteral dosage forms. It will be clear to those skilled in the art that the following dosage forms may comprise as the active component, one or more compounds of formula I, a corresponding pharmaceutically acceptable salt of any of said compounds, or a mixture of such compounds and/or salts.

For preparing pharmaceutical compositions from the compounds described by this invention, inert, pharmaceutically acceptable carriers can be either solid or liquid. Solid form preparations include powders, tablets, dispersible granules, capsules, cachets, and suppositories. A solid carrier can be one or more substances which may also act as diluents, flavoring agents, solubilizers, lubricants, suspending agents, binders, or tablet disintegrating agents; it can also be an encapsulating material. In powders, the carrier is a finely divided solid which is in admixture with the finely divided active compound. In the table the active compound is mixed with carrier having the necessary binding properties in suitable proportions and compacted in the shape and size desired. The powders and tablets preferably contain from 5 to about 70 percent of the active ingredients. Suitable solid carriers are magnesium carbonate, magnesium stearate, talc, sugar, lactose, pectin, dextrin, starch, gelatin, tragacanth, methyl cellulose, sodium carboxymethyl cellulose, a low melting wax, cocoa butter and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets, and capsules can be used as solid dosage forms suitable for oral administration.

Liquid form preparations include solutions, suspensions, and emulsions. As an example may be mentioned water or water-propylene glycol solutions for parenteral injection. Liquid preparations can also be formulated in solution in aqueous polyethylene glycol solution. Aqueous solutions suitable for oral use can be prepared by dissolving the active component in water and adding suitable colorants, flavors, stabilizing, and thickening agents as desired. Aqueous suspensions suitable for oral use can be made by dispersing the finely divided active component in water with viscous material, i.e., natural or synthetic gums, resins, methyl cellulose, sodium carboxymethyl cellulose, and other well-known suspending agents.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules, and powders in vials or ampoules. The unit dosage form can also be a capsule, cachet, or tablet itself or it can be the appropriate number of any of these packaged forms.

The quantity of active compound in a unit dose of preparation may be varied or adjusted from 100 mg to 1,000 mg according to the particular application and the potency of the active ingredient.

In therapeutic use as pharmacological agents the compounds utilized in the pharmaceutical method of this invention are administered at the initial dosage of about 10 mg to about 50 mg per kilogram. A dose range of about 20 mg to about 30 mg per kilogram is preferred. The dosages, however, may be varied depending upon the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired. The daily dosage preferably is in a sustained release form or controlled release form (e.g. an enteric coated or slow release dosage form) to insure that the dosage is released in the intestine or that a uniformly elevated blood level of the methionine compound is achieved.

The active compounds may also be administered parenterally. Solutions of the active compound as a free base or pharmaceutically acceptable salt can be prepared in water suitably mixed with a surfactant such as hydroxypropylcellulose. Dispersions can also be prepared in glycerol, liquid polyethylene glycols, and mixtures thereof and in oils. Under ordinary conditions of storage and use, these preparations contain preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), N,N-dimethylacetamide, suitable mixtures thereof and vegetable oils. The proper fluidity can be maintained, for example, by the use of a coating such as lecithin, by the maintenance of the required particle size in the case of dispersion and by the use of surfactants.

The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by sterilization accomplished by filtering. Generally, dispersions are prepared by incorporating the various sterilized active ingredient into a sterile vehicle which contains the basic dispersion medium and the required other ingredients from those enumerated above. In the case of the sterile powders for the preparation of sterile injectable solutions, the preferred methods of preparation are vacuum drying and the freeze-drying technique which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well-known in the art. Except insofar as any conventional media or agent is incompatible with the active ingredient, its use in the therapeutic compositions is contemplated. Supplementary active ingredients can also be incorporated into the compositions.

It is especially advantageous to formulate parenteral compositions in unit dosage form for ease of administration and uniformity of dosage. Unit dosage forms used herein refers to physically discrete units suitable as unitary dosages for the mammalian subjects to be treated; each unit containing a predetermined quantity of active material calculated to produce the desired therapeutic effect in association with the required pharmaceutical carrier. The specification for the novel unit dosage forms of the invention are dictated by and directly dependent on (a) the unique characteristics of the active material and the particular therapeutic effect to be achieved, and (b) the limitation inherent in the art of compounding such an active material for the treatment of disease in living subjects having a diseased condition in which bodily health is impaired as herein disclosed in detail.

The principal active ingredient is compounded for convenient and effective administration in effective amounts with a suitable pharmaceutically acceptable carrier in unit dosage form as hereinbefore disclosed. A unit dosage form can, for example, contain the principal active compound in amounts ranging from about 250 to about 2,000 mg, with from about 300 to about 1,000 mg being preferred. Expressed in proportions, the active compound is generally present in from about 0.1 to about 500 mg/ml of carrier. In the case of compositions containing supplementary active ingredients, the dosages are determined by reference to the usual dose and the manner of administration of the said ingredients.

The invention and the best mode of practicing the same as illustrated by the following examples of preferred embodiments of selected compounds and their preparation.

| CAPSULES Example 1a d-Methionine 100 mg, 250 mg or 500 mg | |
|---|---|
| d-Methionine | 500 g |
| Lactose USP, Anydrous q.w. or | 200 g |
| Sterotex Powder HM | 5 g |

Combine the methionine and the Lactose in a twin-shell blender equipped with an intensifier bar. Tumble blend for two minutes, blend for one minute with the intensifier bar and then tumble blend again for one minute. A portion of the blend is then mixed with the Sterotex Powder, passed through a #30 screen and added back to the remainder of the blend. The mixed ingredients are then blended for one minute, blended with the intensifier bar for thirty seconds and tumble blended for an additional minute. Appropriate sized capsules are filled with 141 mg., 352.5 mg or 705 mg of the blend, respectively, for the 100 mg., 250 mg and 500 mg containing capsules.

| Example 1b dl-Methionine 100 mg, 250 mg or 500 mg | |
|---|---|
| dl-Methionine | 500 g |
| Lactose USP, Anydrous q.s. or | 200 g |
| Sterotex Powder HM | 5 g |

Mix and fill as per Example 1a.

| TABLETS | |
|---|---|
| The Methionine Compound | 250 g |
| Corn Starch NF | 200.0 g |
| Cellulose, Microcrystalline | 46.0 g |
| Sterotex Powder HM | 4.0 g |
| Purified Water q.s. or | 300.0 ml |

Combine the corn starch, the cellulose methionine compound together in a planetary mixer and mix for two minutes. Add the water to this combination and mix for one minute. The resulting mix is spread on trays and dried in a hot air oven at 50 degrees C. until a moisture level of 1 to 2 percent is obtained. The dried mix is then milled with a Fitzmil through a #RH2B screen at medium speed. The Sterotex Powder is added to a portion of the mix and passed through a #30 screen, and added back to the milled mixture and the total blended for five minutes by drum rolling. Compressed tablets of 100 mg, 500 mg and 1000 mg respectively, of the total mix are formed with appropriate sized punches for the 50 mg, 250 mg or 500 mg containing tablets.

A preferred formulation is one where the total mix is constituted to also contain (1) a pharmaceutically acceptable calcium substance (e.g. calcium carbonate) in unit dosage amount per tablet, (2) betaine, glycine and serine each from 1/10 to 10 times the Met content per tablet, and/or (3) vitamin B12, vitamin B6 and folic acid each from 0.2 to 10 times its recommended daily allowance per tablet.

EXAMPLE 3

Preparation of Intravenous Formulations

A solution of 25g of dl-Methionine is prepared in 1 liter of water for injection at room temperature with stirring. The solution is sterile filtered into 500 5-ml vials, each of which contains 2 ml of solution containing 50 mg of compound, and sealed under nitrogen.

Alternatively, after sterile filtration into vials, the water may be removed by lyophilization, and the vials then sealed aseptically, to provide a powder which is redissolved prior to injection.

We claim:

1. A method for normalizing calcium metabolism in a subject in need thereof, comprising administering to the subject active components in dosage form consisting essentially of a daily allowance of a pharmaceutically acceptable calcium agent which provides 0.5 to 1.5 grams of calcium, an a therapeutically effective calcium metabolism normalizing amount of a methionine compound selected from the group consisting of the methionine hydroxy analog, the S-methyl methionine analog, and methionine compounds having the structural formula I $$CH_3S(CH_2)_n-CH-COOH \quad \quad I$$
$$| $$
$$NH_2$$

dl- or d- form and pharmaceutically acceptable N- (mono- and di-carboxylic acid) acyl derivatives and alkyl esters thereof, where n is an integer from 1 to 3.

2. A method for normalizing body fluid calcium metabolism in a human according to claim 1 but without added calcium where the methionine compound is administered in a daily dosage in the range from 10 to 200 mg/kg of body weight until the calcium metabolism is normalized.

3. A method for treating the condition of hypertension in a subject in need of such treatment, comprising administering to the subject on a daily basis a composition consisting essentially of a pharmaceutically acceptable calcium agent and an effective calcium metabolism normalizing amount of 1 to 5 grams per 70 kg body weight a of methionine compound selected from the group consisting of the methionine hydroxy analog, the S-methyl methionine analog, and methionine compounds having the structural formula I $$CH_3S(CH_2)_n-CH-COOH \quad \quad I$$
$$|$$
$$NH_2$$

dl- or d- form and pharmaceutically acceptable N- (monoand di-carboxylic acid) acyl derivatives and alkyl esters thereof, where n is an integer from 1 to 3, and 0.5 to 5 grams of one of the group consisting of betaine, glycine and serine.

4. A method for inhibiting growth of calculi in a subject in need of said treatment, comprising administering on a daily basis a composition consisting essentially of a pharmaceutically acceptable calcium agent and an effective calcium metabolism normalizing amount of 0.5 to 5.0 grams per 70 kg body weight of a methionine compound selected from the group consisting of the methionine hydroxy analog, the S-methyl methionine analog, and methionine compounds having the structural formula I $$CH_3S(CH_2)_n-CH-COOH \quad \quad I$$
$$|$$
$$NH_2$$

dl- or d- form and pharmaceutically acceptable N- (monoand di-carboxylic acid) acyl derivatives and alkyl esters thereof, where n is an integer form 1 to 3.

5. A method for treating osteoporosis in a subject in need of said treatment, comprising administering to the subject on a daily basis a composition consisting essentially of a pharmaceutically acceptable calcium agent to provide 0.5 to 1.5 grams of calcium per 70 kg body weight and an effective calcium metabolism normalizing amount of a methionine compound of 0.5 to 5.0 grams per 70 kg body weight selected from the group consisting of the methionine hydroxy analog, the S-methyl methionine analog, and methionine compounds having the structural formula I $$CH_3S(CH_2)_n-CH-COOH \quad \quad I$$
$$|$$
$$NH_2$$

dl- or d- form and pharmaceutically acceptable N- (monoand di-carboxylic acid) acyl derivatives and alkyl esters thereof, where n is an integer from 1 to 3.

6. A method for treating osteoporosis according to claim 5 where the methionine compound is administered in a daily dosage ranging from 10 to 200 mg/kg until the calcium metabolism is normalized.

7. A method according to claim 1, claim 4 or claim 5, where the composition further includes at least one homocysteine affecting compound selected from the group comprising betaine, glycine, serine, vitamin B12, vitamin B6, and folate, the homocysteine affecting compound being administered in a therapeutically effective amount for the conversion of excess homocysteine present in the system to methionine, in the case of betaine, and cysteine in the case of other homocysteine affecting compounds.

8. A method according to claim 7 employing a dosage form containing betaine, glycine and serine.

9. A method according to claim 7 employing a dosage form containing vitamin B12, vitamin B6 and folate.

* * * * *